US010582977B2

(12) United States Patent
Morel et al.

(10) Patent No.: US 10,582,977 B2
(45) Date of Patent: Mar. 10, 2020

(54) METHOD AND DEVICE TO ASSIST WITH THE OPERATION OF AN INSTRUMENT

(71) Applicants: Universite Pierre et Marie Curie (Paris 6), Paris (FR); Centre National de la Recherche Scientifique (CNRS), Paris (FR); Endocontrol, La Tronche (FR)

(72) Inventors: Guillaume Morel, Paris (FR); Lin Dong, Shandong (CN); Florian Richer, Sucy en Brie (FR); Nicolas Perrin, Paris (FR); Clément Vidal, Grenoble (FR); Bérengère Bardou, Grenoble (FR)

(73) Assignees: CENTRE NATIONAL DE LA RECHERCHE SCIENTIFIQUE (CNRS), Paris (FR); SORBONNE UNIVERSITE, Paris (FR); ENDOCONTROL, La Tronche (FR)

(*) Notice: Subject to any disclaimer, the term of this patent is extended or adjusted under 35 U.S.C. 154(b) by 253 days.

(21) Appl. No.: 15/548,705

(22) PCT Filed: Feb. 5, 2016

(86) PCT No.: PCT/EP2016/052534
§ 371 (c)(1),
(2) Date: Aug. 3, 2017

(87) PCT Pub. No.: WO2016/124752
PCT Pub. Date: Aug. 11, 2016

(65) Prior Publication Data
US 2018/0028269 A1 Feb. 1, 2018

(30) Foreign Application Priority Data
Feb. 5, 2015 (FR) .................... 15 50921

(51) Int. Cl.
A61B 34/00 (2016.01)
A61B 34/37 (2016.01)
(Continued)

(52) U.S. Cl.
CPC .............. A61B 34/37 (2016.02); A61B 34/30 (2016.02); A61B 34/75 (2016.02); A61B 34/76 (2016.02);
(Continued)

(58) Field of Classification Search
USPC ................................................. 700/245–264
See application file for complete search history.

(56) References Cited

U.S. PATENT DOCUMENTS 6,024,695 A * 2/2000 Taylor .................... A61B 34/20
600/102
6,786,896 B1 * 9/2004 Madhani ................ B25J 9/1615
606/1
(Continued)

FOREIGN PATENT DOCUMENTS

WO WO 2006/124390 A2 11/2006
WO WO-2006124390 A2 * 11/2006 ............ B25J 9/1682

OTHER PUBLICATIONS

International Search Report and Written Opinion in PCT/EP2016/052534 dated Jul. 27, 2016, with English translation coversheet.
(Continued)

Primary Examiner — Jonathan L Sample
(74) Attorney, Agent, or Firm — Womble Bond Dickinson (US) LLP

(57) ABSTRACT

The invention relates to a device and a method to assist with the operation of an instrument by means of said device, the device and the method using leverage effects in order to calculate the data relative to any point of an instrument axis, instead of using low-accuracy sensors. Other improvements
(Continued)

Figure 1:
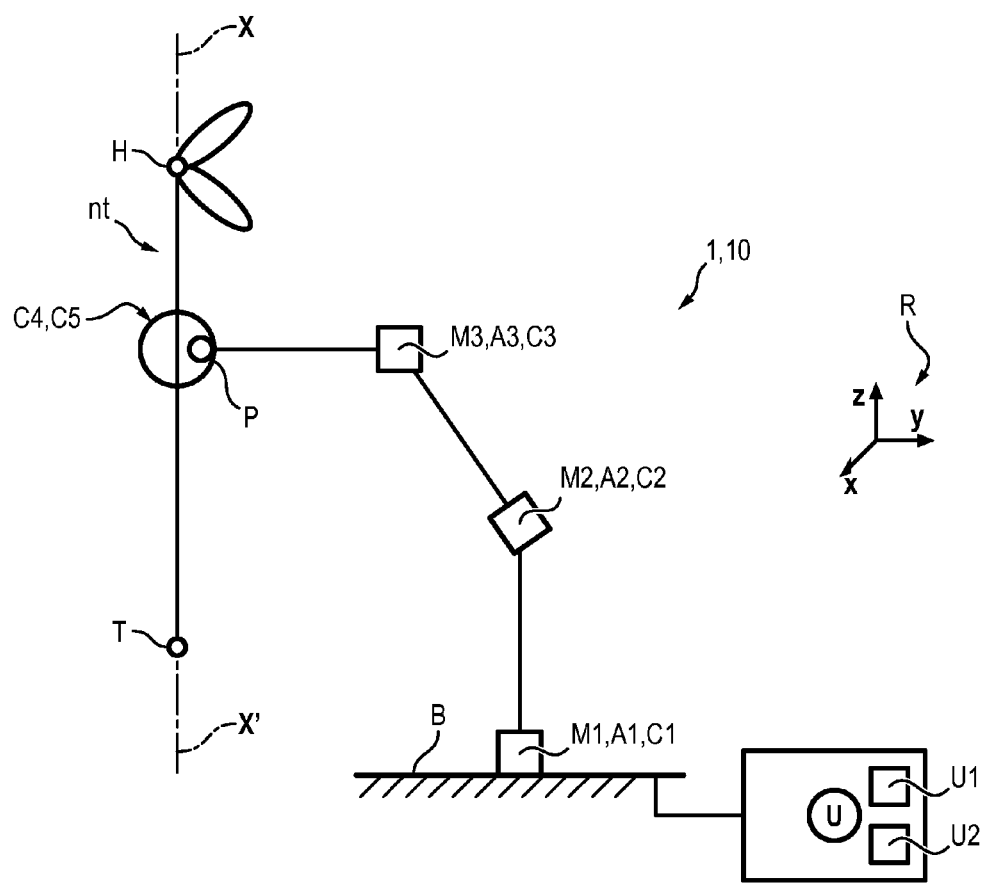

are also described that allow higher-quality usage performance for the operator, which reduces the risk of errors and simplifies the operations.

30 Claims, 7 Drawing Sheets

(51) Int. Cl.
*B25J 18/00* (2006.01)
*A61B 34/30* (2016.01)
*A61B 90/00* (2016.01)

(52) U.S. Cl.
CPC .............. *A61B 34/77* (2016.02); *B25J 18/007* (2013.01); *A61B 2090/062* (2016.02); *A61B 2090/067* (2016.02)

(56) References Cited

U.S. PATENT DOCUMENTS

| | | | |
|---|---|---|---|
| 7,689,320 B2* | 3/2010 | Prisco | A61B 1/00193 700/245 |
| 9,101,397 B2* | 8/2015 | Guthart | A61B 34/30 |
| 9,138,129 B2* | 9/2015 | Diolaiti | A61B 1/00163 |
| 9,333,042 B2* | 5/2016 | Diolaiti | A61B 34/37 |
| 9,345,387 B2* | 5/2016 | Larkin | A61B 1/00087 |
| 9,469,034 B2* | 10/2016 | Diolaiti | A61B 1/00087 |
| 9,622,826 B2* | 4/2017 | Diolaiti | B25J 9/161 |
| 9,795,446 B2* | 10/2017 | DiMaio | A61B 34/10 |
| 9,901,408 B2* | 2/2018 | Larkin | B25J 9/1671 |
| 2007/0192910 A1* | 8/2007 | Vu | B25J 5/007 700/245 |
| 2009/0024142 A1* | 1/2009 | Ruiz Morales | A61B 34/76 606/130 |
| 2009/0036902 A1* | 2/2009 | DiMaio | A61B 34/10 606/130 |
| 2010/0087835 A1* | 4/2010 | Blumenkranz | A61B 90/10 606/130 |
| 2010/0204713 A1* | 8/2010 | Ruiz Morales | A61B 34/30 606/130 |
| 2011/0155784 A1* | 6/2011 | Shelton, IV | A61B 17/07207 227/176.1 |
| 2011/0174862 A1* | 7/2011 | Shelton, IV | A61B 17/07207 227/176.1 |
| 2013/0131867 A1* | 5/2013 | Olds | B25J 9/0051 700/260 |
| 2013/0190774 A1* | 7/2013 | Beira | A61B 34/72 606/130 |
| 2013/0304258 A1* | 11/2013 | Taylor | B25J 9/1689 700/260 |
| 2014/0052150 A1* | 2/2014 | Taylor | A61F 9/00727 606/130 |

OTHER PUBLICATIONS

Search Report in French Application No. 15 50921 dated Jun. 2, 2016, with English translation coversheet.

* cited by examiner

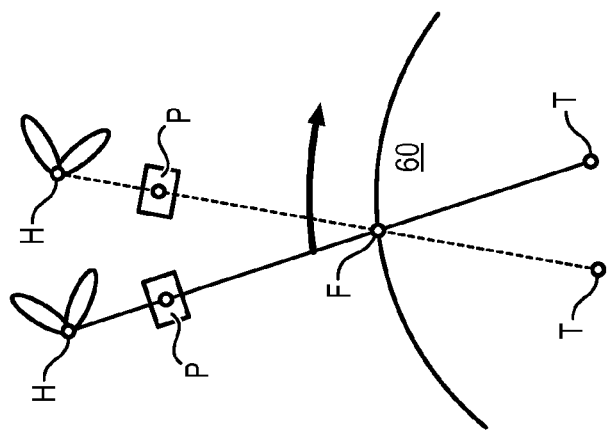
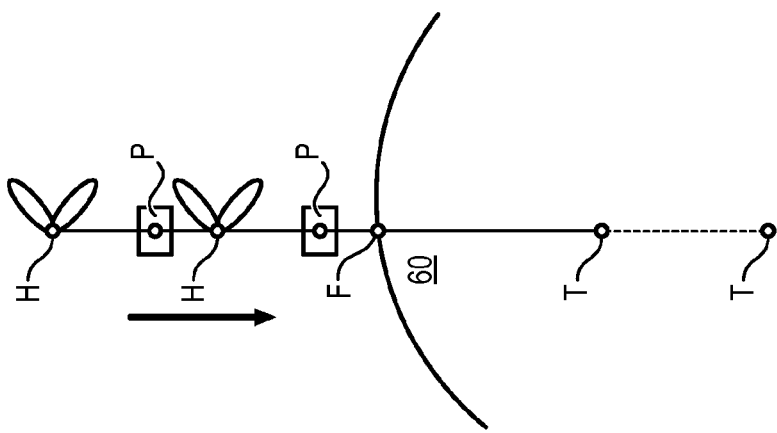
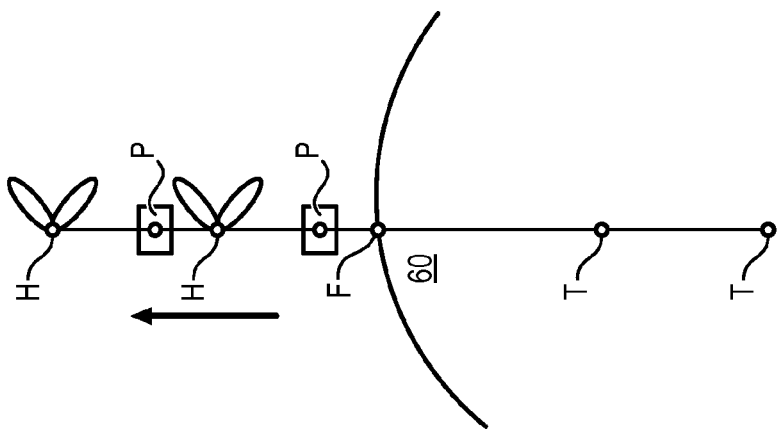

METHOD AND DEVICE TO ASSIST WITH THE OPERATION OF AN INSTRUMENT

GENERAL TECHNICAL FIELD

The invention relates to co-manipulation robotics, that is the simultaneous manipulate of an instrument by a robot and by an operator in order to assist the operator manipulating the instrument. Here the word instrument designates an object in the general sense, which can be a tool, a mechanical part, a visualization device such as a camera, etc. The user carries out a task which consists of manipulating this object and the co-manipulation robot has the role of assisting him.

The invention relates more precisely to the methods and devices for assisting in the manipulation of an instrument passing through an opening, the distal end whereof must be monitored. Such devices or methods are advantageously used in cooperation with video monitoring provided by an endoscope, so that the operator can directly observe his operations.

The invention finds application particularly in application to laparoscopic surgery for which long and thin instruments are inserted (via cannulas) into the body of a patient so as to allow surgical intervention.

This type of operation generally requires several instruments and can last several hours.

PRIOR ART

In the present text, the examples will be given for the surgical field. However, they can be applied without difficulty to any kind of operation through an opening and requiring equipment similar to that of a laparoscopy (precision mechanics, etc.).

In the absence of a device for assisting in manipulating an instrument, such as a robot bearing an instrument, all instruments are manipulated by the surgeon and/or an assistant. Laparoscopic surgery generally imposes accurate and technical actions, as well as a difficult and sustained body posture for the operator, which can cause musculoskeletal impairment.

One evolution of this surgery is directed toward telemanipulated robotics, wherein the robot which bears the instruments is controlled at a distance by a surgeon. Besides the elevated cost of such a robot, there exist considerable limitations. For example, the fact that the manipulating surgeon is not "sterile" can be mentioned (he works at a non-sterile console), or even that the peri-surgical operations are complicated (the surgeon must indicate exactly which instruments he desires at which place, because he is not directly onto the body of the patient), or even the fact that such a robot can operate only for very localized operations (prostate, uterus, etc.) but does not make it possible to operate effectively when it is necessary to reach zones of the body distant from one another, for example when it is necessary to change the cannula (the device allowing insertion of the instrument into the patient).

Another evolution, which is that which affects the invention, is directed toward co-manipulation of a tool by means of a robot and of an operator. The robot, in this case, besides the fact that it bears instruments, makes it possible to filter the inaccuracies of the actions of the operator (vibrations, etc.).

Filtration methods use for example a viscosity, in establishing a relation between a displacement velocity and a force, or even a stiffness, in establishing a relation between a position deviation and a force, or in attributing a virtual inertia to the instrument. Combinations of these effects can also be required. The set of these effects and of their possible combinations are included in the mechanical impedances which can be achieved by the robot thanks to programming media.

As shown in FIG. 1, the assistance devices 1 for co-manipulation of an instrument have three active degrees of freedom, which can be accomplished for example thanks to three successive actuators A1, A2, A3 each of which controls one axis, which makes it possible for a given point of the final end of the robot controlled by these actuators to be displaced in the three spatial dimensions. It is possible, without changing the principle of the invention, to organize the three actuators in parallel and not in series, according to the principles of parallel robotics known to a person skilled in the art. It is also possible to use more than three actuators to displace a given point of the last end of the robot, thus constituting a redundant kinematic chain, according to the principles of redundant robots known to a person skilled in the art. In addition, these devices have three passive degrees of freedom, thanks to a passive ball joint positioned on said end. The latter cannot therefore transmit torque and allows the free operation of the instrument 20 by an operator. Furthermore, the instrument 20 is inserted so that the axis of the instrument 20 passes through the center of the passive ball joint. An attachment point P is defined which passes through the center of the ball joint and which passes through the instrument 20.

The device is controlled by a processing unit U. The general architecture consists of recovering information (generally position, velocity) from the instrument 20, processing them and determining a force to apply to the attachment point.

Sensors C1, C2, C3 are arranged at each actuator (hence three sensors) and two sensors C4, C5 are arranged at the ball joint for measuring rotations other than that performed around the axis of the instrument. In other words, C4 and C5 make it possible to measure the orientation of the instrument axis. To implement the device, it is not necessary to know the rotation of the instrument on its own axis.

Figure 3:
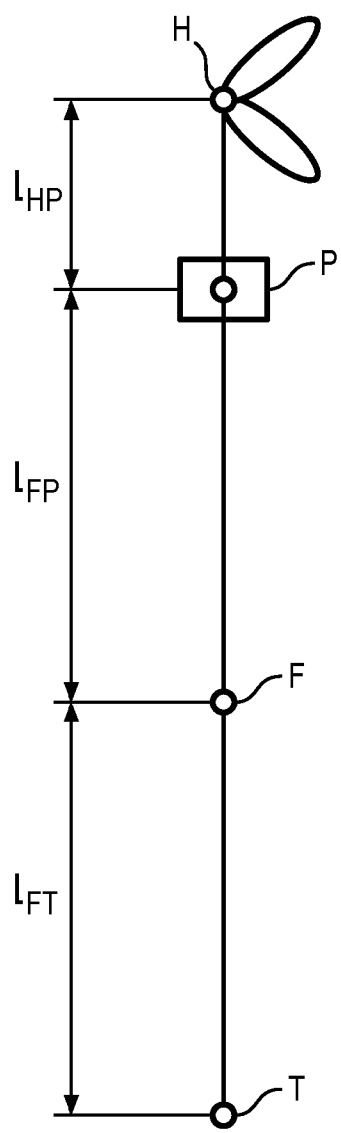

In fact, the points of interest which are the center of the ball joint, the position of the hand of the operator or the tip of the instrument (or distal end of the instrument) are all situated on the axis of the instrument. FIG. 3 illustrates the positioning of these points.

But co-manipulation devices currently have limitations which impair their use or which prevent better use of the possibilities that they could confer.

Certain of these limitations are the following.

As mentioned previously, impedances are implemented to improve the sensations of the operator during manipulation and also for improving his actions.

One known solution is to create an impedance at the center of the ball joint, which is facilitated by the fact that the position of the center of the ball joint is precisely known at each instant thanks to the three sensors C1, C2 and C3 present at the three actuators.

But this solution is not optimal from the point of view of the operator's sensations, and it can be preferable to create a programmable impedance at the instrument's grasping handle (in the operator's hand) or at the distal end of the instrument, which is the portion that the operator wishes to control.

But to program an impedance at the other points, it is necessary, according to the prior art, to use the sensors C4 and C5 of the ball joint in addition to the sensors C1, C2 and C3 of the hinges.

For technical reasons, the sensors of the actuators offer an accurate signal with little noise while the sensors of the ball joint (typically potentiometers) can be of lower quality and offer a low-accuracy signal with a good deal of noise.

Consequently, knowledge of the data relating to other points of the axis of the instrument (the distal end of the instrument or a point on the proximal handle for example) such as the position or the velocity is relatively poor, which does not allow the desired impedance to be had at the desired point.

Another problem which occurs in co-manipulation robotics for assistance in laparoscopic surgery (or more generally in manipulation through an opening) resides in the configuration of the robot and in particular the configuration of the incision point, which is the entry point of the instrument into the body of the patient.

Certain existing robots for assisting in laparoscopic surgery operate about a fixed point. The robot must then be precisely positioned, before the operation, so as to have said fixed point correspond with the incision point.

An adjustment procedure, carried out prior to the beginning of the operation, is necessary.

Such procedures are subject to errors, and slow down the flow of the intervention. It is therefore desirable to propose devices which require neither precise positioning of the robot, nor adjustment.

Another problem is found in the application of the impedances and the perceptions of the operator. In the case of viscosity, which establishes a relation between a force and a velocity (to give the impression to the surgeon of moving within a viscous medium), it is suitable for the operator, for light and accurate motions, to work with high viscosity to filter out all his inaccuracies despite the low velocities; on the other hand, when he must move the instrument to another zone of the patient, he must work with low viscosity, otherwise he will have to exert a high force to simply move the tool, which can cause unnecessary fatigue and loss of time, the robot slowing the action.

To this end, it has already been proposed to generate a viscosity that is variable between two states (low when the hand velocity is high, high when the hand velocity is low), or continuous.

Figure 4:
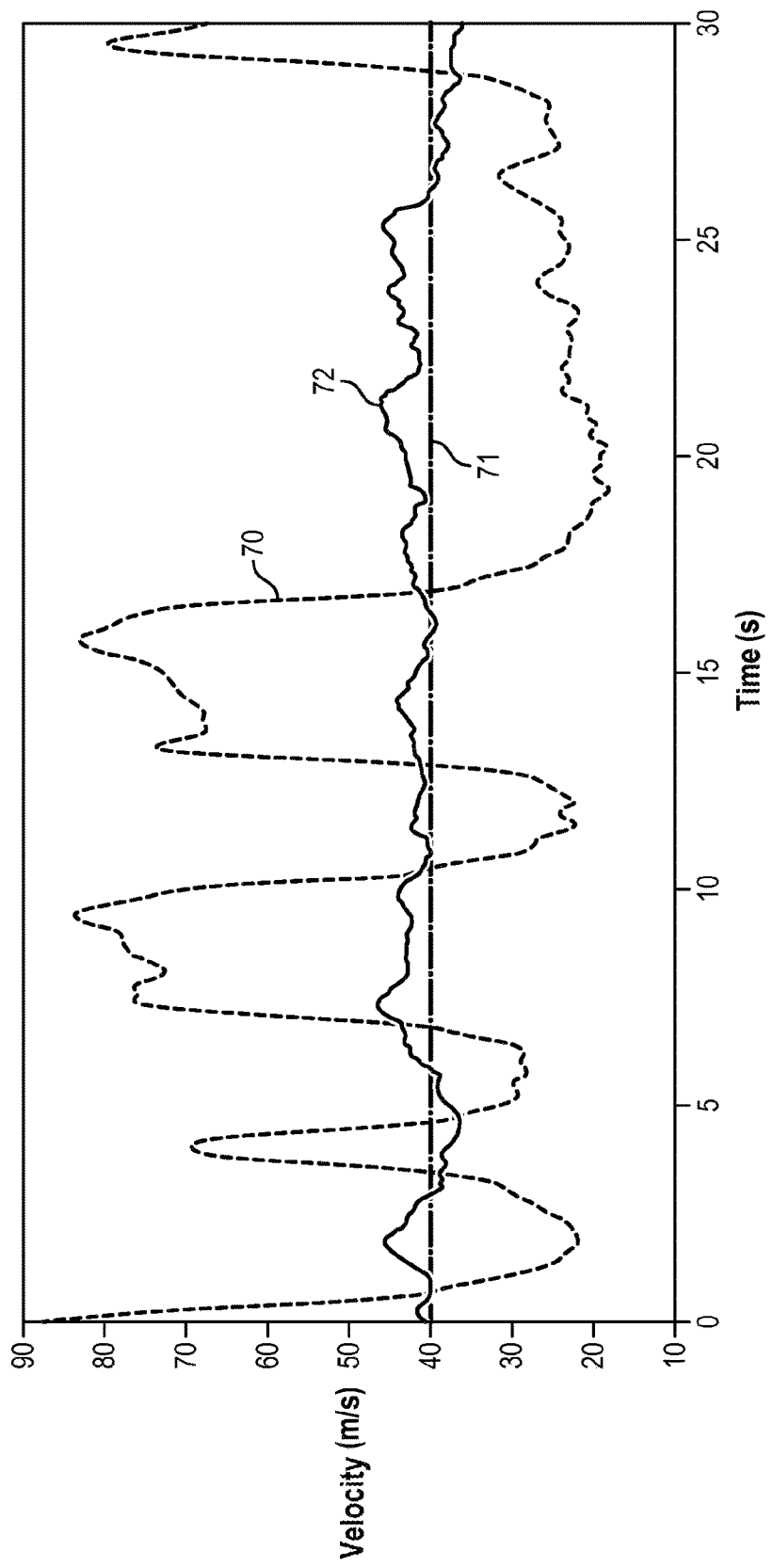

Such configurations can generate instabilities, as has been reported in an experimental test illustrated in FIG. 4: here the operator wishes to move the instrument at an average velocity which corresponds to an intermediate viscosity between the maximum value (for low velocities) and the minimum value (for high velocities). To attain this average velocity, starting from zero velocity, the operator will push hard to accelerate the movement. When velocity increases, the drop in viscosity will lead to a reduction in the resistance of the robot, which will have the effect of drastically accelerating the movement; consequently the velocity will rapidly increase beyond the average velocity at which the operator wishes to move the instrument. The operator then reduces his thrust to slow down, which will lead to an increase in viscosity and drastically decelerate the movement: an oscillation is thus generated around the average velocity desired by the user, which prevents correct use of the co-manipulation system.

To offer to the operator a co-manipulation robot which helps him in a more directed manner, it is possible to define guides. To this end, it is first necessary to define geometric constraints (a point, a straight line, a sphere, etc.). The co-manipulation robot is then programmed to apply forces designed to move the point of the instrument onto this constraint, or on the other hand to repel a point of the instrument when it approaches this constraint. A method known in the prior art is to use elastic forces (that is proportional to the displacement with respect to the constraint) which is a particular form of mechanical impedance. This is particularly interesting, within the scope of the intended application, if the point of the instrument is its distal end, because that makes it possible to guide this end, for example to avoid a given anatomical region or to hold the end in a resection plane. In this case, it is possible to define the constraint relative to the anatomy of the patient, then to calculate this constraint in the coordinate system of the robot using a known adjustment method. But this operation is complex because it requires planning and an adjustment.

Finally, as operations last several hours, it happens that the operator is not strictly speaking manipulating the instrument. For example, he may wish to rest his arm, or carry out another action with another instrument. It also happens that the manipulation consists simply of holding the position and the orientation of the instrument constant. That is the case for example when the instrument is a retractor with which the operator is lifting (or retracting) an organ so as to leave free access to a portion of the anatomy that it covers. In these different specific cases, it is desirable that the co-manipulation robot be able to enter a mode named locked mode, which consists simply of immobilizing the instrument without the operator's assistance. Switching into a locked mode, or more generally switching from one mode of operation (with a given impedance) to another (with another impedance) is generally accomplished by using an appended control means such as a button, a pedal, a voice command or any other means. The integration of said control is problematic in numerous situations: the hands of the surgeon are occupied by the instruments, which makes the use of manual control complex; his feet are often occupied by the pedals of various devices, such as those of the imaging systems or of the electro-surgical instruments; his voice is used to communicate with the rest of the team and the cognitive load of verbal communication with a machine, using specific wording, can be distracting. It is therefore desirable that the co-manipulation robot be capable of "guessing" into which mode the operator wishes it to switch to accomplish this switching.

Presentation of the Invention

One aim of the invention is to propose a method of assistance allowing an increase in the accuracy of the action of the operator when he operates the device and to propose said device in particular.

According to a first aspect, this aim is achieved thanks to a method to assist with the manipulation of an instrument by means of an assistance device in manipulating the instrument, the device comprising a hinged arm designed to be attached to a frame and manipulable by an operator, to which an instrument can be attached at an attachment point of said hinged arm forming a passive ball joint between the hinged arm and the instrument, the hinged arm comprising motors for displacing the attachment point in a reference frame bound to the frame, the instrument being operable around a fulcrum having a known and fixed position in the reference frame, a processing unit comprising a processor configured to control the motors so as to produce a given impedance at any point of an instrument axis connecting the attachment point to the fulcrum;

the method being characterized in that it comprises the steps consisting of:

determining data relating to a position and/or a velocity of the attachment point in the reference frame bound to the assistance device;

determining a force to be applied to the attachment point as a function of said data relating to the attachment point, the position of the fulcrum, and the known distance from the attachment point to an arbitrary point, and on a given impedance to be conferred to the arbitrary point, controlling the motors to transmit said force to the instrument at the attachment point.

Thanks to such a method, it is not necessary to obtain the data provided by the angular sensors at the passive ball joint and it is possible to use only the data provided by the actuator sensors, the measurements whereof are accurate and noise free (see introduction). For this purpose, one solution consists of using a lever model around the fulcrum of the instrument, the position whereof is known. This fulcrum is typically situated at the cannula (previously inserted for example into the abdominal wall of the patient), into which the instrument is slipped.

Knowing the data relating to the attachment point and the position of the fulcrum, which is fixed, it is possible to produce a given impedance at any point of the axis, as will be explained in the detailed description of the invention.

According to a second aspect, the invention relates to a method for automatic adjustment during assistance in manipulating an instrument by means of an assistance device in manipulating the instrument, the device comprising a hinged arm designed to be attached to a frame and operable by an operator, to which an instrument can be attached at an attachment point of said hinged arm forming a passive ball joint between the hinged arm and the instrument, the hinged arm comprising hinges and sensors measuring displacement, said arm making it possible to displace the attachment point in a reference frame bound to the frame, the instrument having an instrument axis with a known direction, a processing unit comprising a processor configured to control the motors;

the method being characterized by the steps consisting of:

obtaining, in the reference frame bound to the device, a plurality of straight lines defined by the instrument axis, the straight lines corresponding to a plurality of configurations of the instrument, estimating the existence of an intersection zone of said plurality of straight lines, obtaining the central position of said zone if it exists, said zone corresponding to a fulcrum of the instrument.

Such a method is self-configured because it is not necessary to launch a configuration routine prior to the use of the instrument. In fact, as long as the operator has not inserted the instrument into a cannula (which forms a fulcrum for the instrument), no intersection zone is detected and it is considered that there is no fulcrum. One of the consequences can be: holding in free mode, with no particular impedance applied, or with a low viscosity. On the other hand, as soon as the operator inserts the instrument into a cannula, the processor automatically detects an intersection zone and identifies a fulcrum with its coordinates.

The lack of accuracy of the position of the fulcrum due to the sensors (in particular the sensors of the passive ball joint) is overcome by the multitude of measurements taken. Thus, using averaging or filtering, it is possible to obtain, quasi-continuously, an accurate value, with little noise, for this position.

The frequency of the measurements is on the order of a millisecond, which signifies that in less than a second, several hundred equations have been obtained. In this manner, the co-manipulation is usable quasi-instantaneously, even when the operator has just inserted the instrument into the cannula.

Moreover, the method can operate continuously, so as to constantly estimate the zone of intersection of the straight lines. Thus, the system will be able to quickly detect when an operator withdraws the instrument from a cannula, or places it in another cannula, or even when the center of the cannula is displaced during the operation, for example when the patient is repositioned by the operator.

The advantage of the method is then mainly characterized in that it does not require a special adjustment procedure, but is accomplished continuously, with no particular intervention by the operator.

According to a third aspect, the invention relates to a method to assist with the manipulation of an instrument by means of an assistance device in manipulating the instrument, the device comprising, a hinged arm designed to be attached to a frame and manipulable by an operator, to which an instrument can be attached at an attachment point of said hinged arm, comprising motors for displacing the attachment point in a reference frame bound to the frame, a processing unit comprising a processor configured to control the motors;

the method being characterized in that it comprises the steps consisting of:

determining the instantaneous velocity of a point of the instrument in the reference frame bound to the assistance device;

determining a first decreasing viscosity function of said instantaneous velocity, determining a second viscosity from the first viscosity thanks to a filtering method having at least one parameter allowing the dynamics of the method to be regulated determining a force at said point of the instrument, a function:

of said instantaneous velocity, and of the second viscosity value, controlling motors to transmit said force to the instrument at the attachment point.

Filtering the viscosity makes it possible to decrease the variations of force when the velocity varies and thus to eliminate the effects of instability.

The measurement of the velocity can itself be advantageously filtered when it has considerable noise.

The method can advantageously be applied to a device comprising a passive ball joint the center whereof coincides with the attachment point and such that the instrument passes through a fixed point. In this case, the calculation point of the velocity and of the forces of the method can be either said attachment point or another point of the instrument axis. In the case where the method is applied to a point of the instrument axis which is not the attachment point, the first aspect of the invention can advantageously be combined with the third aspect of the invention to avoid the use of sensors integrated in the passive ball joint in the calculation of velocities and forces.

According to a fourth aspect, the invention relates to a method to assist with the manipulation of an instrument by means of an assistance device in manipulating the instrument,
the device comprising
a hinged arm designed to be attached to a frame and manipulable by an operator, to which an instrument can be attached at an attachment point of said hinged arm, the hinged arm comprising motors for displacing the attachment point in a reference frame bound to the assistance device, said instrument having a point of interest,
a processing unit comprising a processor configured to control the motors;
the method being characterized in that it comprises the steps consisting of:
causing the point of interest to coincide with points in space and determining the position of said points in space in the reference frame bound to the assistance device;
constructing a geometric constraint defined by said points in space by means of said positions.

The point of interest of the instrument can advantageously be its distal end, the method then coming down, for the operator, to pointing points in space with the distal end of the instrument. These points are those which the operator considers to be the point serving to define the geometric constraint.

The geometric constraint can take any form which can be defined by an equation which the point of interest must then verify. In addition, according to this fourth aspect of the invention, a step consisting of determining a force at the point of interest of the instrument using a determination of the distance between the point of interest of the instrument, determined at any instant during the operation, and the geometric constraint (plane, sphere, point, etc.) by orthogonal projection can then be provided, the force at the point of interest being a function of a stiffness coefficient and said distance. In this manner, the control of the motors constrains the instrument to position itself with respect to the plane by causing the attraction or the repulsion of said point of interest with respect to said plane. It can be necessary, for this purpose, to calculate a force at the attachment point as a function of the force at the point of interest, for example when the device has a passive ball joint and the instrument runs through a fixed point. The calculations are then carried out in a similar fashion to what is described in the first aspect of the invention, by selecting as an arbitrary point the point of interest of the instrument.

According to a fifth aspect, the invention relates to a method to assist with the manipulation of an instrument by means of an assistance device in manipulating the instrument,
the device comprising
a hinged arm designed to be attached to a frame and manipulable by an operator, to which an instrument can be attached at an attachment point of said hinged arm, the hinged arm comprising motors for displacing the attachment point in a reference frame bound to the frame,
a processing unit comprising a processor configured to control the motors,
a plurality of control modes implemented in the processing unit by the processor, characterized by predetermined impedances;
the method being characterized in that it comprises steps consisting of switching automatically from one control mode to another when a criterion is verified.

Advantageously, said criterion will use only measurements supplied by the hinged arm.

In particular, two control modes can be implemented:
a locked mode for which a predetermined locking impedance is applied to the instrument and guarantees holding the instrument in position,
a free mode for which a predetermined free impedance is applied to the instrument and allows its operation by the operator.

In this case, the locking criterion can be an immobility of the instrument for a predetermined period and the unlocking criterion can be a translation of the instrument along an instrument axis.

The methods according to the different aspects can advantageously be implemented alone or in combination so as to correct the limitations of the prior art presented in the introduction.

In addition, the invention proposes an assistance device for manipulating an instrument, said device being configured, by means of a processing unit, for implementing one of the methods described previously.

As previously indicated, these methods and devices find application in any field of robotics requiring considerable accuracy in operation.

PRESENTATION OF THE FIGURES

Figure 2:
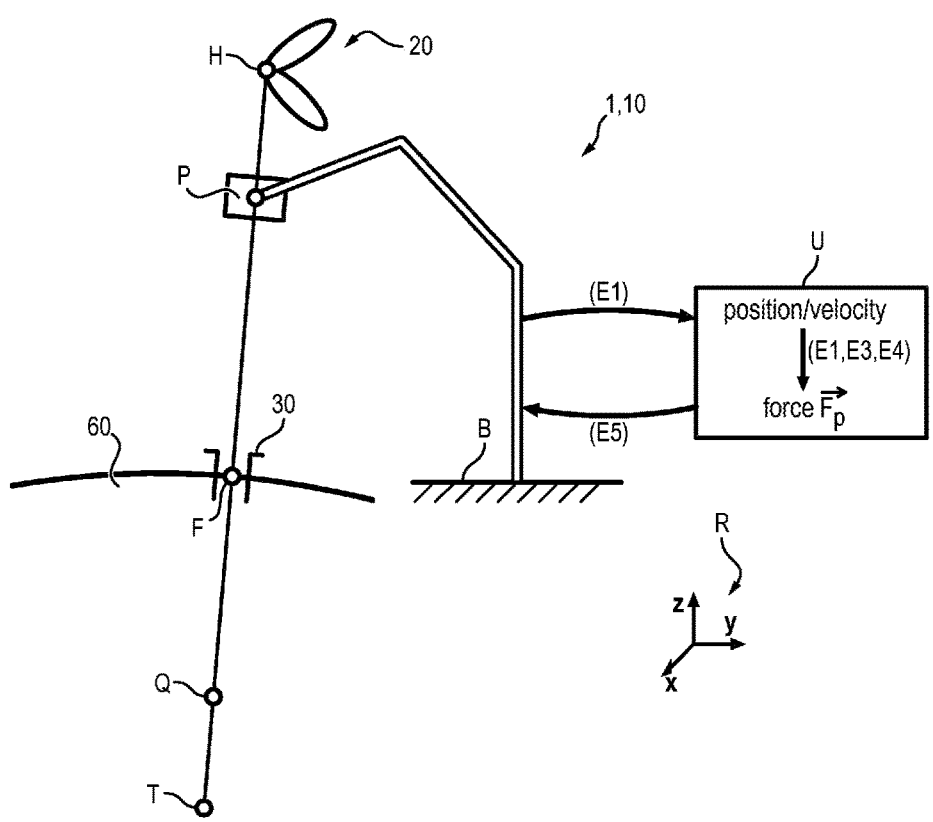
Figure 5A:
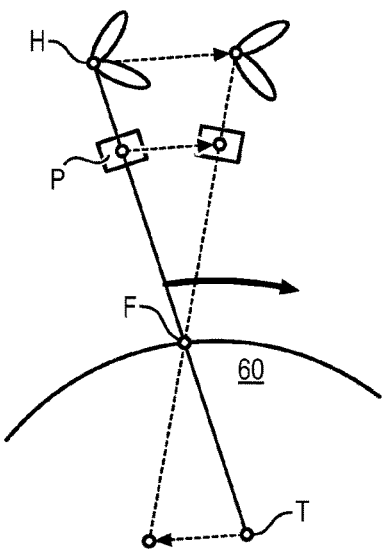
Figure 5B:
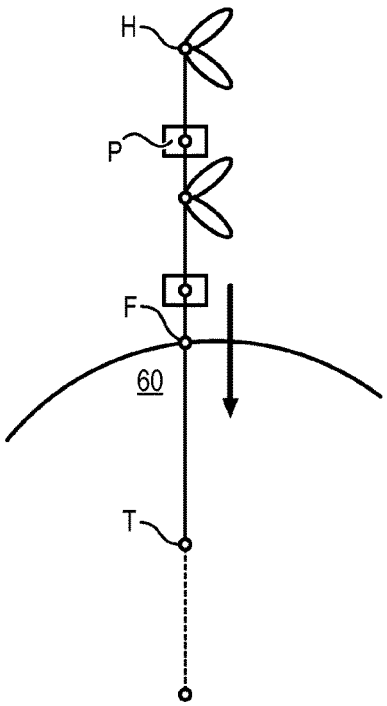
Figure 6:
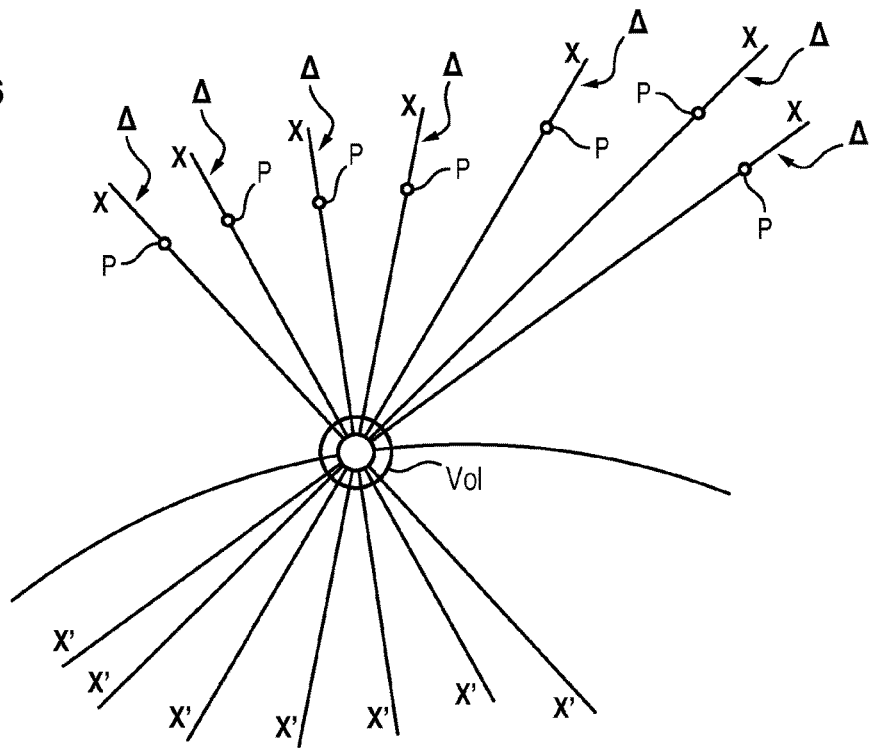
Figure 7:
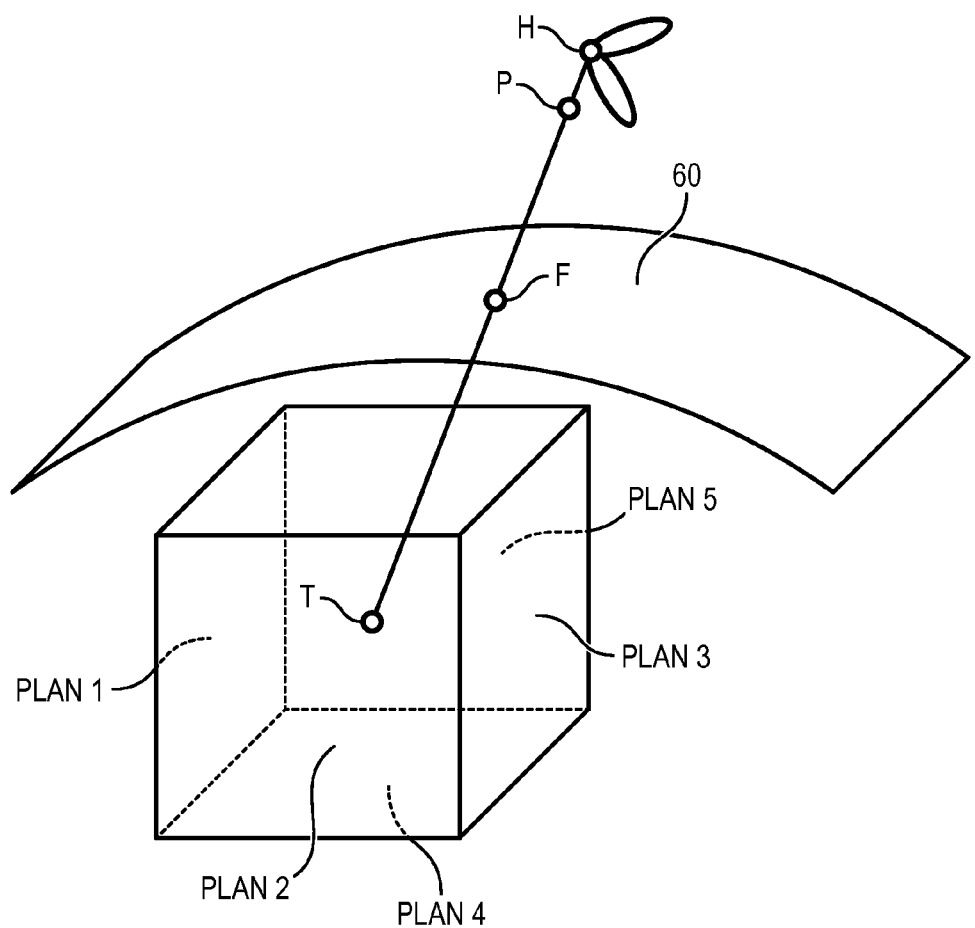

Other features, aims and advantages of the invention will be revealed by the description that follows, which is purely illustrative and not limiting, and which must be read with reference to the appended drawings, wherein:

FIG. 1 is a schematic representation of an assistance device conforming to one embodiment of the invention, FIG. 2 is a schematic representation illustrating flows of information passing within the device, FIG. 3 illustrates different characteristic points of an instrument manipulated by means of the device, FIG. 4 illustrates the velocity of the attachment point with different models of viscosity, for an instrument manipulated with the device, FIGS. 5a and 5b illustrate different manipulation positions using the device, with in particular one tangential displacement per lever arm of the instrument, and one translation displacement, FIG. 6 illustrates a plurality of straight lines passing through a cannula in which is inserted an instrument manipulated by means of the device, FIG. 7 illustrates a set of planes defied by means of the device, FIGS. 8a, 8b and 8c illustrate unlocking criteria for a locked mode of the device.

In all the figures, similar elements bear identical numerical references.

DETAILED DESCRIPTION

In the present application, the positions are defined with respect to a reference frame bound to the frame to which the device is attached, which means that the robot can be displaced without any reconfiguration being necessary.

As shown in FIG. 1, one embodiment of the assistance device 1 comprises a hinged arm 10 attached to a frame B. An instrument 20 is attached to an attachment point P of said arm.

The instrument 20 is co-manipulated by an operator and by the device 1. This can for example be a laparoscopic surgical instrument such as a needle holder, a clamp or scissors.

The hinged arm 10 is driven by three motors M1, M2, M3, at the three hinges A1, A2, A3, which makes it possible to move the attachment point P in three degrees of freedom in translation in a reference frame R bound to the frame B.

The hinged arm can, thanks to its motors M1, M2, M3, bring the attachment point P anywhere in space within the reach of the device 1.

Consequently, the hinged arm 10 is adapted to transmit a force in the three spatial directions at the attachment point P.

It is possible to use more than three motors and three hinges to position the point P and transmit a force to point P.

According to the first aspect of the invention, the connection at the attachment point P is a connection of the passive ball joint type.

Consequently, the hinged arm 10 cannot transmit a moment at point P to the instrument 20, which is free to rotate around the point P with respect to the hinged arm 10.

This connection can be accomplished for example by three successive bodies, each of the bodies being connected to the body preceding it by a pivot connection and the axes. In this case, the axis of the instrument X-X' can advantageously coincide with the axis of the last pivot.

A processing unit U, comprising a processor U1 and a storage memory U2, controls the motors M1, M2, M3 and processes the different data relating to the use of the device 1.

The instrument 20 has an elongated shape and extends along a principal axis called the instrument axis X-X'.

Sensors C1, C2, C3, at each of the three hinges make it possible to know the movement of each hinge and as a result, thanks to the processing unit U, to know the position of the attachment point P. This knowledge can be quasi-continuous.

It is technically possible to use in these hinges sensors which offer very good accuracy and little noise. In fact, generally, the motorized hinges have a transmission stage which increases torque while reducing velocity. Thus, a sensor placed on the motor shaft will have a greater resolution than if it had to be placed directly on the output shaft of the hinge.

Advantageously, the device 1 comprises at least two angular position sensors C4, C5 at the attachment point P which measure, in combination with the sensors C1, C2, C3, the orientation of the instrument axis X-X' in the reference frame bound to the frame B. Only two sensors are necessary because the rotation of the instrument 20 along its instrument axis X-X' does not change the orientation of the instrument axis X-X'. When the passive ball joint is implemented with three successive pivot connections, the axis of the last pivot connection coinciding with the instrument axis X-X', it is advantageous to use C4 to measure the angle of the first pivot connection and C5 to measure the angle of the second pivot connection.

For technical reasons, these angular sensors C4, C5 offer a low-accuracy, noisy signal. It is currently difficult to implement better-quality sensors at this location because, to increase resolution, it would be necessary for example to integrate a reduction stage which would increase the volume and the weight of the passive ball joint device.

For example, the angular sensors C4, C5 are generally potentiometers.

In addition, it is possible to provide another sensor C6 which measures the rotation of the instrument 20 on its axis X-X'. This makes it possible to calculate, in combination with C1, C2, C3, C4 and C5, the position of any points of the instrument which would not be on the instrument axis X-X'. This has an advantage in surgery for example in the case of oriented or flexible instruments.

In the same manner, it is possible to provide a motor M6 applying a torque along the instrument axis X-X', which makes it possible, in combination with the motors M1, M2 and M3, and in the case where the instrument axis X-X' passes through a known fixed fulcrum F, to apply forces at any point of the instrument which does not belong to its axis X-X'.

The instrument 20 is adapted to penetrate into the body of a patient 60 at a cannula 30. The cannula 30 serves as a fulcrum F around which the instrument is manipulated.

Consequently, at the cannula 30, the instrument 20 is free to slip in translation, and free to pivot around the fulcrum F defined by the cannula 30.

By definition, the fulcrum F is substantially fixed in the base B but can move along the instrument 20 during operations.

Several points of interest can be observed on such an instrument 20 (see FIG. 3):

The attachment point P, presented previously, wherein the hinged arm can transmit forces (no torque), and reciprocally, The point relating to the handle H ("hand"), which corresponds to the place where the operator is holding the tool, that is the proximal end of the instrument, The point relating to the tip T, which corresponds to the distal end of the instrument and which acts on the patient, The fulcrum F, presented previously.

To improve the utilization rendering to the operator, the assistance device 1 makes it possible to apply impedances to the instrument, that is it simulates a viscosity, a stiffness or an inertia (or a combination) applied to the instrument 20 and which the operator must feel.

Ultimately, the device applies forces to the instrument 20 at the attachment point P.

The position and/or the velocity observed on the instrument 20 are sent to the processing unit U, which in exchange sends a force to be applied (see FIG. 2).

The applicable impedances depend on several parameters, such as the utilization mode or the gesture that the operator is carrying out.

A viscosity $\mu$ is an impedance which relates a force to a velocity:

$$\vec{F} = -\mu \vec{v}$$

A stiffness k is an impedance which relates a force to a deviation with respect to a reference position (depending on the sign of the stiffness, a return force or a repulsion force will result):

$$\vec{F} = k(\vec{x}_0 - \vec{x})$$

A mass m is an impedance which relates a force to an acceleration:

$$\vec{F} = -m\frac{d\vec{v}}{dt}$$

There are different pre-established laws, which determine which impedance values apply. These impedance values can for their part be functions of the position or of the velocity of a point on the instrument 20.

As mentioned in the introduction, the attachment point P which corresponds directly to the force application point of the device 1 to the instrument 20 seems to be the natural point for applying an impedance.

Yet, for the purpose of improving the use of the device 1, it is possible for example to decide that the stiffness felt by the operator be the same at the handle H, regardless of the position of the fulcrum F on the instrument 20, that is to say regardless of the depth of insertion of the instrument 20 into the body of the patient.

Consequently, it is necessary to be able to define the viscosity practically at every instant at the point relating to the handle H.

Another example can be taken: it is possible to wish to define the viscosity at the point T.

In any case, to apply a force which is relevant and helps the operator to manipulate the instrument 20, it is necessary to obtain data relating to the position or to the velocity of these points (H or T or another point of the instrument axis X-X'), which are different from the attachment point P.

Lever Arm Method

One of the proposed methods makes it possible to obtain these data for an arbitrary point Q located on the instrument axis X-X'. For this purpose, it is assumed that the instrument 20 is installed in the cannula 30 and has said fulcrum F. Consequently, the instrument axis X-X' passes through the attachment P and fulcrum F points.

It is also assumed that the position of the fulcrum F is known. There exist several methods for knowing this position. It is possible for example to carry out a calibration routine beforehand, or enter the coordinates, or apply a method which will be described later.

The method for obtaining said data of a point located on the instrument axis X-X' consists of carrying out the following steps, by means of the processing unit U:

determining E1 data relating to a position and/or a velocity of the attachment point P in the reference frame bound to the device 1, determining E2 velocity or position data of a point Q of the instrument 20 located on the instrument axis X-X' using said data relating to the attachment point P, the known distance $\overline{PQ}$ of the attachment point P to the arbitrary point Q on the instrument axis X-X', and the position of the fulcrum F, which is known, determining E3 a force $\vec{F}_Q$ by means of an impedance to be conferred to the instrument at said point Q of the instrument 20, and by means of the data determined in step E2 of said point Q of the instrument 20, determining E4 a force $\vec{F}_P$ to be applied to the attachment point P by means of the foregoing force $\vec{F}_Q$ at the arbitrary point Q, and by means of data relating to the attachment point P and to the position of the fulcrum F, controlling E5 motors M1, M2, M3 to transmit the force $\vec{F}_P$ to be applied to the attachment point P of the instrument at the attachment point P.

The step E1 thus comprises data acquisition coming from the sensors with processing by the processing unit U, steps E2 through E4 are steps consisting of processing by the processing unit U, and finally step E5 comprises instructions for actuating motors.

Such a method does not require knowing the orientation of the axis of the instrument 20, and consequently does not require using the angular sensors C4, C5 at the ball joint of the attachment point P.

As mentioned previously, such sensors are of bad quality, contrary to the sensors C1, C2, C3 of the hinges A1, A2, A3, which offer an accurate signal with little noise.

During step E2, to determine the position of the point Q from the position of the point P, the position of the point F, and the distance d=$\overline{PQ}$ from P to Q along the instrument axis X-X', it is possible to proceed in the following fashion: calculate first the unit vector $\vec{x}_I$ from the instrument axis X-X':

$$\vec{x}_I = (1/\|\overrightarrow{PF}\|)\overrightarrow{PF},$$

then calculate the position of the point Q with respect to the point P:

$$\overrightarrow{PQ} = d\vec{x}_I.$$

During the same step E2, knowing the position of the point P, the velocity of the point P, the position of F, and $\vec{x}_I$ makes it possible to calculate the velocity of a given point Q of the instrument axis located at a known distance d=$\overline{PQ}$ from P, thanks to a lever model known to a person skilled in the art:

$$\vec{v}(Q) = (\vec{v}(P) \cdot \vec{z}_I)\vec{z}_I + \left(\frac{\overline{FQ}}{\overline{FP}}\right)(\vec{v}(P) - (\vec{v}(P) \cdot \vec{z}_I)\vec{z}_I),$$

where $\overline{FP}$ and $\overline{F_Q} = \overline{FP} + d$ are the signed distances from the points F to P and from F to Q respectively.

In a dual fashion, during step E4, knowing the force $\vec{F}_Q$ which would need to be applied to the point Q makes it possible, thanks to a lever model known to a person skilled in the art, to apply the force equivalent to that to be applied to the point P:

$$\vec{F}_P = (\vec{F}_Q \cdot \vec{x}_I)\vec{x}_I + \left(\frac{\overline{FQ}}{\overline{FP}}\right)(\vec{F}_Q - (\vec{F}_Q \cdot \vec{x}_I)\vec{x}_I)$$

For a pure rotation movement around the fulcrum F, the knowledge of the lever arm and of a velocity of a single point (point P) is sufficient (see FIG. 5a). For a translation movement along the axis X-X', all the points of the instrument 20 have the same velocity (see FIG. 5b).

FIG. 3 presents the distances which occur in the calculations, in particular the lengths $l_{HP}$, $l_{PF}$ and $l_{PT}$ if the point Q corresponds to the handle or the tip.

Once the force that needs to be applied to the arbitrary point Q is obtained, the lever arm makes it possible to recover the force that the motors M1, M2, M3 must apply to the attachment point P.

The following logical chain is obtained, when for example the impedance involves only the velocity:

$$\vec{v}(P) \xrightarrow{E2 \text{ (lever)}} \vec{v}(Q) \xrightarrow{E3 \text{ (impedance at } Q)} \vec{F}_Q \xrightarrow{E4 \text{ (lever)}} \vec{F}_P$$

According to a preferred embodiment, the point Q corresponds to the point T relating to the tip, or to the point H relating to the handle.

This has an advantage in the quality of the interaction. For example, of the impedance is a simple coefficient of viscosity and the arbitrary point Q coincides with the point T, then by this method an isotropic viscosity will be obtained at point T, that is to say that the force at T, $\vec{F}_T$, will always be parallel to the velocity of T, $\vec{v}(T)$ to which it opposes.

On the other hand, if the arbitrary point Q coincided with the point P, as it is conventional to proceed without invoking steps (E2) and (E4), then there would be an isotropic viscosity at point T, that is to say that the force at T, $\vec{F}_T$, would not necessarily be parallel to the velocity of T, $\vec{v}(T)$.

Moreover, the detailed three-step calculations above can be applied, after reformulation, in a single step in which the velocity of Q $\vec{v}(Q)$ and the force to be applied to the arbitrary point Q do not appear explicitly, which amounts to writing a direct function relating the position and the velocity of the attachment point P to the force to be applied to the attachment point P, using only the knowledge of the position of F, the impedance to be applied at the arbitrary point Q, and the distance defining the known position of the point Q on the instrument axis X-X'.

Consequently, steps E2 through E4 can be reduced to a processing step wherein a force to be applied to the attachment point is determined as a function of said data related to the attachment point, and the known distance from the attachment point P to the arbitrary point Q, for the purpose of conferring a given impedance to the arbitrary point Q.

Self-Calibration Method

First of all, the self-calibration method makes it possible to know if the instrument 20 is actually positioned in a cannula 30 and therefore possesses a fulcrum F and, if so, to know the position of said fulcrum F.

It is assumed that the processing unit U can know the equation of the axis of the instrument. This is made possible thanks to the five sensors of the hinged arm C1, C2, C3, C4, C5.

It is recalled again that it is not necessary to have a sixth sensor.

The method comprises the following steps:
Obtaining E01, in the reference frame of the device, a plurality of straight lines Δ defined by the instrument axis X-X', the straight lines corresponding to a plurality of configurations of the instrument,
Estimating E02 the existence of an intersection zone $V_{ol}$ of said plurality of straight lines Δ,
obtaining E03 the central position of said zone $V_{ol}$ if it exists, said zone then corresponding to the fulcrum F of the instrument.

In this method, it is not necessary to have motors M1, M2, M3. In fact, to know said straight lines, it is sufficient to have sufficient sensors, in the present case the five sensors C1 through C5.

FIG. 6 shows in superposition straight lines resulting from a displacement of said instrument 20. As illustrated in this figure, they intersect at a zone corresponding to the fulcrum F.

In fact, the lack of accuracy of the angular sensors C4, C5 is compensated by the plurality of the measurements taken, either due to averaging or to filtering, or to both. The acquisition time is on the order of a millisecond, which means that in one second approximately, a sufficient quantity of information is assembled to obtain a reliable result as to the existence or not of an intersection zone and its possible position.

Algorithms for solving a linear matrix system are known in the literature. In particular, due to the inaccuracy of the measurements and the lack of complete immobility of the cannula 30, the intersection zone is a volume $V_{ol}$. Depending on the selected criteria (size, etc.), it is possible to validate or not the presence of a fulcrum.

For example, the resolution of the linear system can be accomplished by a least squares approach.

The position of the fulcrum F corresponds for example to the center of such a volume $V_{ol}$.

Practically, when the operator seizes the instrument, the unit U calculates at regular intervals the equation of the straight line Δ of the instrument axis X-X' (every millisecond for example). The unit U can also wait, before calculating a new straight line equation, not for a given time but for a given displacement of the point P to ensure that all the straight lines are not superimposed. As long as the operator has not inserted the instrument 20 into the cannula 30, the unit U will not find an intersection zone and consequently will not know that the instrument 20 is not inserted into a cannula 30.

Once the operator has inserted the instrument 20 into a cannula 30, the unit U determines, with a time scale on the order of a second, the existence of such a zone and thus knows the position of the fulcrum F.

The method can comprise a supplementary step E05 of applying a force at the fulcrum P using a predetermined impedance, when no intersection zone is identified.

It is possible for example to apply a fairly low viscosity to the attachment point P in such a manner that the operator easily moves the instrument 20.

This method for automatically detecting the fulcrum F, unlike pre-existing routines, does not need to be carried out beforehand. The operator can thus directly use the instrument 20.

This provides important advantages:
when the patient moves, or when the operator causes the patient to move (a shock to the operating table), the position of the fulcrum F changes and the device 1 can then alert the operator to it,
when the operator changes cannulas 30, there is no need to carry out a new calibration, hence a time saving and a reduction in risk.

Such a method can be used independently of the lever arm method described previously.

Filtered Viscosity Model Method

This method relates to the case where the impedance is a viscosity and it is desired to avoid the effects of instability mentioned in the introduction (see curve 70 in FIG. 4, with respect to the reference curve 71).

It is assumed that the position of a point Q is known (to that end, it is possible if necessary to use the method mentioned above during the description of the lever arm method).

The method comprises the following steps:

(E1') determining the instantaneous velocity $\vec{v}(Q)$ of a point Q of the instrument 20 in the reference frame bound to the assistance device 1, (E21') determining a first viscosity which is a decreasing function of said instantaneous velocity $\vec{v}(Q)$, (E22') determining a second viscosity from the first viscosity thanks to a filtering method having at least one parameter allowing the dynamics of the method to be regulated, (E3') determining a force $\vec{F}_Q$ at said point Q of the instrument 20, a function:

of said velocity $\vec{v}(Q)$, of the second viscosity value,

Finally, the step of controlling the motors is conventional.

When the point Q is different from the attachment point P, the lever arm model can be used both for calculating the velocities ($\vec{v}(P) \Rightarrow \vec{v}(Q)$) and for calculating the forces ($\vec{F}_Q \Rightarrow \vec{F}_P$).

If the velocity signal $\vec{v}(Q)$ is noisy, it is possible to add a step consisting of filtering said velocity $\vec{v}(Q)$ between step E1' and step E21'.

Such a method slows the dynamics of the viscosity variation and offers a stability not previously possible (see curve 72 in FIG. 4).

The configurable coefficient is typically a time constant which can be adjusted to optimize the dynamics of the method.

Such a method can be used independently of the lever arm and self-calibration methods described previously.

Pointing Instrument Method

Another method will now be described. Likewise, it can advantageously be applied in combination with the method allowing a force to be applied to the attachment point P.

For example, it is desired to establish a geometric constraint using elastic force fields, such as an attraction or repulsion plane, to establish a guide for the instrument 20. For example, if a zone in the patient must not be reached, being able to define a repulsion plane makes it possible to limit the risks for the operator.

More generally, to establish the constraint a point of interest of the instrument is defined: this point of interest is advantageously its distal end.

To this end, the method comprises the following steps:

have the point of interest coincide E01' with points in space and determine E02' their position in the reference frame bound to the assistance device 1, construct E03' a geometric constraint defined by said points in space by means of said positions.

When the point of interest is the distal end, the method consists, for the operator, in designating points in space with said end.

Once this is accomplished, it is possible to define several types of geometric constraints.

For example, the geometric constraint can be a plane, and in this case it is advantageous to point three non-coplanar points, the plane then being determined as that which passes through said three points.

The geometric constraint can also be a straight line, and in this case it is advantageous to point two distinct points, the straight line then being determined as that which passes through said two points.

The geometric constraint can also be a sphere, and in this case it is advantageous to point two distinct points, the sphere then being defined as being that whose center is the first of said two points and which passes through the second of said two points.

The constraint can be reduced to a single point, and in this case it is advantageous to define it by pointing directly to this point.

Several planes PLAN1, . . . , PLAN 5 are shown in FIG. 7, defining a space wherein the instrument is prompted to remain (repulsion planes), by using an appropriate stiffness for each of the planes PLAN1, . . . , PLAN 5.

In this example, the point of interest defined for the pointing method and the arbitrary point Q defined by the lever arm method are the same unique point. The method then comprises the following steps following the determination of the plane:

determination E31' of the distance between said point Q of the instrument 20 and the plane PLAN1, by orthogonal projection, determination E32" of the force $\vec{F}_Q$ at said point Q, said force $\vec{F}_Q$ being a function of a stiffness coefficient and of said distance.

The steps consisting of determining the force E4 at the attachment point P and of controlling E5 the motors M1, M2, M3 are those conventionally used or those previously described.

Change of State Method

This method makes it possible to improve the comfort and the intuitiveness of the use of the device for the operator.

To that end, the processing unit U has been configured to comprise several control modes, each control mode having a predetermined impedance and a predetermined switching criterion.

The method consists of switching between modes when one predetermined switching criterion is verified.

Automatic switching is then obtained requiring no action other than the operation of the instrument by the operator.

Advantageously, the predetermined criteria depend only on the measurements supplied by the hinged arm.

The changing method can be applied at any time during the other methods described.

According to one embodiment, the method consists of changing state between two control modes called the locked mode (designed to hold the instrument in position even if the operator lets it go) and the free mode (designed to leave the operator free to manipulate the instrument).

The method can then comprise the following steps:

verification E6 of a locking criterion and switching into locked mode for which a predetermined locking impedance is applied to the instrument, if the verification is positive, verification E7 of an unlocking criterion and switching into free mode for which a predetermined free impedance is applied to the instrument, if the verification is positive.

One advantageous embodiment defines the free impedance as a low-value viscosity to allow its manipulation by the operator and/or the locking impedance comprises a sufficiently high stiffness to guarantee that the instrument will be held in position.

The other methods, described previously, can then be applied.

One advantageous embodiment defines the locking criterion as an immobility for a predetermined period (three seconds for example) and the unlocking criterion as a "departing" translation of the instrument along the instrument axis X-X' (see FIG. 8a). These two criteria are independent. Two movements which, in the present case, would not unlock the locked mode are shown in FIGS. 8b and 8c.

The invention claimed is:

1. A method to assist with the manipulation of an instrument by means of an assistance device (1) in manipulating the instrument (20),
the device (1) comprising
a hinged arm (10) designed to be attached to a frame (B) and manipulable by an operator, to which an instrument (20) can be attached at an attachment point (P) of said hinged arm (10) forming a passive ball joint between the hinged arm (10) and the instrument (20), the hinged arm comprising motors (M1, M2, . . .) for displacing the attachment point (P) in a reference frame (R) bound to the frame (B), the instrument (20) being manipulable around a fulcrum (F) having a known and fixed position in the reference frame (R),
a processing unit (U) comprising a processor (U1) configured to control the motors (M1, M2, . . .);
the method being characterized in that it comprises the steps of:
determining (E1) data relating to a position and/or a velocity of the attachment point (P) in the reference frame (R);
determining (E2, E3, E4) a force ($\vec{F_P}$) to be applied to the attachment point (P) as a function of said data relating to the attachment point, the position of the fulcrum, the known distance ($\overline{PQ}$) from the attachment point (P) to an arbitrary point of an instrument axis connecting the attachment point (P) to the fulcrum (F), and a given impedance to be conferred to the arbitrary point (Q),
controlling (E5) the motors (M1, M2, . . .) to transmit the force ($\vec{F_P}$) to the instrument (20) at the attachment point (P) so as to produce the impedance at the arbitrary point (Q).

2. The method according to claim 1, wherein the step of determining the force (Fp) to be applied to the attachment point comprises the following steps:
determining (E2) data regarding the velocity and/or the position of a point (Q) of the instrument situated on an instrument axis (X-X') passing through the attachment point (P) and the fulcrum (F), by means of said data relating to the attachment point (P) and the position of the fulcrum (F);
determining (E3) a force ($\vec{F_Q}$) to be applied to the point Q as a function of an impedance to be conferred to the instrument (20) at said point (Q) of the instrument (20) and as a function of the data determined regarding said point (Q) of the instrument (20);
determining (E4) a force ($\vec{F_P}$) to be applied to the attachment point (P) as a function of the force ($\vec{F_Q}$) to be applied to the arbitrary point and the data relating to the attachment point P and to the position of the fulcrum (F).

3. The method according to claim 1, wherein the impedance comprises a viscosity and the force ($\vec{F_P}$) applied to the attachment point (P) is a resistance force in the opposite direction to its displacement.

4. The method according to claim 1, wherein the impedance comprises a stiffness and the force ($\vec{F_P}$) applied to the attachment point (P) is a force in the same direction or in the opposite direction to its displacement, depending on the sign of the stiffness.

5. The method according to claim 4, wherein the position of the attachment point (P) in the reference frame (R) is determined by means of sensors (C1, C2, C3) in the hinged arm (10), the hinged arm comprising three hinges (A1, A2, A3) each actuated by a motor (M1, M2, M3) and each comprising one of the sensors (C1, C2, C3).

6. The method according to claim 1,
wherein the direction of the instrument axis (X-X') is known, the method comprising a preliminary step (E0) of determining the position of the fulcrum (F) in said reference frame (R), and the following sub-steps
obtaining (E01), in the reference frame, a plurality of straight lines (Δ) defined by the instrument axis (X-X'), the straight lines corresponding to a plurality of positions of said instrument (20) around the fulcrum (F),
estimating (E02) an intersection zone ($V_{oi}$) of said plurality of straight lines (Δ),
obtaining (E03) the position of the center of said zone ($V_{oi}$), which corresponds to the fulcrum (F).

7. The method according to claim 6, wherein the orientation of the instrument axis (X-X') is obtained by means of two angular position sensors (C4, C5) at the attachment point (P).

8. The method according to claim 1, wherein the impedance comprises a viscosity, and wherein the step (E3) of determining the force (Fq) at said point (Q) comprises the following sub-steps for determining the impedance to be conferred:
determining (E1') the instantaneous velocity ($\vec{v}(Q)$) of said point (Q) of the instrument,
determining (E21') a first viscosity as a decreasing function of said instantaneous velocity ($\vec{v}(Q)$),
determining (E22') a second velocity from the first viscosity thanks to a filtering method having at least one parameter allowing the dynamics of the method to be regulated;
determining (E3') the force at said point of the instrument, as a function:
of said velocity ($\vec{v}(Q)$), and
of the second viscosity value allowing the dynamics of the method to be adjusted.

9. The method according to claim 8, wherein the instantaneous velocity of the point (Q) is filtered.

10. The method according to claim 1, wherein the method comprises:
having a point of the instrument coincide (E01') with points in space and determining the position of said points in space in the reference frame bound to the assistance device;
constructing (E03') a geometric constraint defined by said points in space by means of said positions.

11. The method according to claim 10, wherein the impedance comprises a stiffness, the method comprising a preliminary step of constructing a plane, said point of the instrument being a distal end, said step comprising the following sub-steps:
pointing (E01') with the distal end to at least three non-collinear points and determination of their position, and determination (E02') of their position in the reference frame (R),
construction (E03') of a plane (PLAN1) passing through the three points by means of the three positions,
the step (E3) of determining the force ($\vec{F_P}$) at the attachment point (P) comprising the following sub-steps:

determining (E31") the distance between said point (Q) of the instrument (20) and the plane by orthogonal projection, determining (E32") the force ($\vec{F_Q}$) as a function of a stiffness and of said distance, so that the step (E5) of controlling the motors constrains the instrument to position itself with respect to the plane (PLAN1) by causing the attraction or the repulsion of said point (Q) of the instrument axis (X-X') with respect to said plane (PLAN1).

12. The method according to claim 1, wherein a plurality of switching modes is implemented in the processing unit (U), each mode having a predetermined impedance, the method comprising switching automatically from one control mode to another when a criterion is verified.

13. The method according to claim 12, wherein said at least one criterion only involves the data relating to the assistance device (1).

14. The method according to claim 13, wherein two impedances are configured to define respectively a free mode and a locked mode, wherein a locking criterion makes it possible to transition from the free mode to the locked mode and an unlocking criterion makes it possible to transition from the locked mode to the free mode.

15. The method according to claim 14 wherein the locking criterion is an immobility of the instrument (20) for a predetermined period and the unlocking criterion is a translation of the instrument (2) along the instrument axis (X-X').

16. A device to assist with the manipulation of an instrument (20), comprising:
  a hinged arm (10) designed to be attached to a frame (B) and operable by an operator, to which an instrument (20) can be attached at an attachment point (P) of said hinged arm (10) forming a passive ball joint between the hinged arm (10) and the instrument (20), the hinged arm comprising motors (M1, M2, . . . ) for displacing the attachment point (P) in a reference frame (R) bound to the frame (B), the instrument (20) being operable around a fulcrum (F) having a known and fixed position in the reference frame (R),
  a processing unit (U) comprising a processor (U1) configured to control the motors (M1, M2, . . . );
  the device being characterized in that it is configured for determining (E1) the data relating to a position and/or a velocity of the attachment point (P) in the reference frame (R);
  and in that the processing unit is configured to implement the steps of determining (E2, E3, E4) a force ($\vec{F_P}$) to be applied to the attachment point (P) as a function of said data relating to the attachment point, the position of the fulcrum, the known distance ($\overline{PQ}$) from the attachment point (P) to an arbitrary point of an instrument axis connecting the attachment point (P) to an arbitrary point of an instrument axis connecting the attachment point (P) to the fulcrum (F), and a given impedance to be conferred to the arbitrary point (Q),
  the device also being configured to control (E5) the motors (M1, M2, . . . ) to transmit the force ($\vec{F_P}$) to the instrument (20) at the attachment point (P), so as to produce the impedance at the arbitrary point (Q).

17. The device according to claim 16, wherein the processing unit (U) is configured to implement the step of determining the force ($\vec{F_P}$) to be applied to the attachment point in the following manner:

determining (E2) data regarding the velocity and/or the position of a point (Q) of the instrument situated on an instrument axis (X-X') passing through the attachment point (P) and the fulcrum (F), by means of said data relating to the attachment point (P) and the position of the fulcrum (F);

determining (E3) a force ($\vec{F_Q}$) to be applied to the point Q as a function of an impedance to be conferred to the instrument (20) at said point (Q) of the instrument (20) and as a function of the data determined regarding said point (Q) of the instrument (20);

determining (E4) a force ($\vec{F_P}$) to be applied to the attachment point (P) as a function of the force ($\vec{F_Q}$) to be applied to the arbitrary point and the data relating to the attachment point P and to the position of the fulcrum (F).

18. The device according to claim 16, configured so that the impedance comprises a viscosity and the force ($\vec{F_P}$) applied to the attachment point (P) is a resistance force in the opposite direction to its displacement.

19. The device according to claim 16, configured so that the impedance comprises a stiffness and the force ($\vec{F_P}$) applied to the attachment point (P) is a force in the same direction or in the opposite direction to its displacement, depending on the sign of the stiffness.

20. The device according to claim 19, wherein the hinged arm (10) comprises three hinges (A1, A2, A3) each actuated by a motor (M1, M2, M3) and each comprising a sensor (C1, C2, C3) so as to determine the position of the attachment point (P) in the reference frame (R).

21. The device according to claim 16, wherein the direction of the instrument axis (X-X') is known, and wherein the processing unit (U) is configured to implement a preliminary step (E0) of determining the position of the fulcrum (F) in said reference frame (R) in the following manner:
  obtaining (E01), in the reference frame, a plurality of straight lines (Δ) defined by the instrument axis (X-X'), the straight lines corresponding to a plurality of positions of said instrument (20) around the fulcrum (F),
  estimating (E02) an intersection zone ($V_{oi}$) of said plurality of straight lines (Δ),
  obtaining (E03) the position of the center of said zone ($V_{oi}$), which corresponds to the fulcrum (F).

22. The device according to claim 21, wherein the device (1) comprises two angular position sensors (C4, C5) at the attachment point (P) for obtaining the orientation of the instrument axis (X-X').

23. The device according to claim 16, wherein the processing unit (U) is configured so that the impedance comprises a viscosity, and wherein the step (E3) of determining the force (Fq) at said point (Q) is implemented in the following manner to determine the impedance to be conferred:

determining (E1') the instantaneous velocity ($\vec{v}(Q)$) of said point (Q) of the instrument,
  determining (E21') a first viscosity as a decreasing function of said instantaneous velocity ($\vec{v}(Q)$),
  determining (E22') a second viscosity from the first viscosity thanks to a filtering method having at least one parameter allowing the dynamics of the method to be regulated;
  determining (E3') the force at said point of the instrument, as a function:

of said velocity ($\vec{v}(Q)$), and
of the second viscosity value allowing the dynamic to be adjusted.

24. The device according to claim 23, wherein the processing unit (U) is configured so that the instantaneous velocity at the point (Q) is filtered.

25. The device according to claim 16, wherein the processing unit (U) is also configured to implement the steps of:
    having a point of the instrument coincide (E01') with points in space and determining the position of said points in space in the reference frame bound to the assistance device;
    constructing (E03') a geometric constraint defined by said points in space by means of said positions.

26. The device according to claim 25, wherein the processing unit (U) is configured so that the impedance comprises a stiffness, and wherein the processing unit is configured to implement a preliminary step of constructing a plane, said point of the instrument being a distal end, said step comprising the following sub-step:
    pointing (E01') with the distal end to at least three non-collinear points and determination of their position, and determination (E02') of their position in the reference frame (R),
    construction (E03') of a plane (PLAN1) passing through the three points by means of the three positions, the step (E3) of determining the force ($\vec{F_P}$) at the attachment point (P) comprising the following sub-steps:
    determining (E31") the distance between said point (Q) of the instrument (20) and the plane by orthogonal projection,
    determining (E32") the force ($\vec{F_Q}$) as a function of a stiffness and of said distance,
    so that the step of controlling (E5) the motors constrains the instrument to position itself with respect to the plane (PLAN1) by causing the attraction or the repulsion of said point (Q) of the instrument axis (X-X') with respect to said plane (PLAN1).

27. The device according to claim 16, wherein a plurality of switching modes is implemented in the processing unit (U), each mode having a predetermined impedance, the processing unit (U) being configured to implement steps of switching automatically from one control mode to another when a criterion is verified.

28. The device according to the claim 27, wherein at least one criterion only involves the data relating to said assistance device in the implementation of the method.

29. The device according to claim 28, wherein the processing unit (U) is configured to implement two impedances which are configured to define respectively a free mode and a locked mode, and implement a locking criterion which to transition from the free mode to the locked mode and an unlocking criterion to transition from the locked mode to the free mode.

30. The device according to claim 29 wherein the locking criterion is an immobility of the instrument (20) for a predetermined period and the unlocking criterion is a translation of the instrument (20) along the instrument axis (X-X').

* * * * *